US00RE43141E

(19) United States
(12) Reissued Patent
Halseth et al.

(10) Patent Number: US RE43,141 E
(45) Date of Reissued Patent: Jan. 24, 2012

(54) FLUID COLLECTION DEVICE HAVING TILTING RETRACTABLE NEEDLE

(75) Inventors: Thor R. Halseth, Simi Valley, CA (US); Michael J. Botich, Oxnard, CA (US); Robert T. McWethy, Ventura, CA (US); Bradley M. Wilkinson, North Haledon, NJ (US); William Saulenas, Wayne, NJ (US); Michelle Sullivan, Lebanon, NJ (US)

(73) Assignee: MDC Investment Holdings, Inc., Salt Lake City, UT (US)

(21) Appl. No.: 11/787,232

(22) Filed: Apr. 13, 2007

Related U.S. Patent Documents

Reissue of:

(64) Patent No.: 6,524,276
Issued: Feb. 25, 2003
Appl. No.: 09/588,151
Filed: Jun. 5, 2000

(51) Int. Cl.

| | |
|---|---|
| ***A61M 5/00*** | (2006.01) |
| ***A61B 5/00*** | (2006.01) |
| ***B65D 81/00*** | (2006.01) |
| ***A61M 5/32*** | (2006.01) |

(52) U.S. Cl. ..... 604/110; 600/573; 600/576; 604/181; 604/187; 604/192; 604/197; 604/198; 604/263

(58) Field of Classification Search ..... 128/919; 600/573, 576, 577, 583; 604/110, 171, 181, 604/187, 192, 197, 198, 199, 200, 201, 205, 604/244, 263

See application file for complete search history.

(56) References Cited

U.S. PATENT DOCUMENTS

| | | | | | |
|---|---|---|---|---|---|
| 4,770,655 | A | * | 9/1988 | Haber et al. | 604/110 |
| 4,813,426 | A | | 3/1989 | Haber et al. | |
| 4,838,863 | A | * | 6/1989 | Allard et al. | 604/110 |
| 4,846,808 | A | * | 7/1989 | Haber et al. | 604/195 |
| 4,883,466 | A | * | 11/1989 | Glazier | 604/110 |
| 4,892,107 | A | * | 1/1990 | Haber | 600/576 |
| 4,908,022 | A | * | 3/1990 | Haber | 604/195 |
| 4,909,794 | A | * | 3/1990 | Haber et al. | 604/195 |
| 4,915,702 | A | * | 4/1990 | Haber | 604/198 |
| 4,932,940 | A | * | 6/1990 | Walker et al. | 604/110 |
| 4,986,813 | A | * | 1/1991 | Blake et al. | 604/110 |
| 5,019,044 | A | * | 5/1991 | Tsao | 604/110 |
| 5,085,640 | A | * | 2/1992 | Gibbs | 604/110 |
| 5,122,118 | A | * | 6/1992 | Haber et al. | 604/110 |
| 5,181,524 | A | * | 1/1993 | Wanderer et al. | 600/577 |
| 5,193,552 | A | | 3/1993 | Columbus et al. | |
| 5,211,629 | A | * | 5/1993 | Pressly et al. | 604/110 |
| 5,273,540 | A | * | 12/1993 | Luther et al. | 604/110 |
| 5,336,198 | A | * | 8/1994 | Silver et al. | 604/195 |
| 5,346,480 | A | * | 9/1994 | Hess et al. | 604/197 |

(Continued)

*Primary Examiner* — Kevin C Sirmons
*Assistant Examiner* — Shefali Patel
(74) *Attorney, Agent, or Firm* — Rutan & Tucker, LLP

(57) ABSTRACT

A medical device is provided for collecting fluid samples from a patient, such as blood samples. The device includes a needle having a forward sharpened tip that is retracted into the housing of the device after use to prevent exposure to the contaminated needle. The rearward end of the housing is open, forming a socket for receiving a fluid container, such as a vacuum tube, that will receive the fluid sample. A needle retainer releasably retains the needle in the extended position against the rearward bias of a biasing element. After use, the medical professional retracts the needle by pressing an actuation button, allowing the biasing element to displace the needle rearwardly. A guide track guides the needle during retraction, tilting the needle off-axis.

31 Claims, 4 Drawing Sheets

U.S. PATENT DOCUMENTS 5,382,235 A * 1/1995 Sak ..... 604/110
5,393,301 A * 2/1995 Goldberg ..... 604/110
5,407,436 A * 4/1995 Toft et al. ..... 604/195
5,433,703 A * 7/1995 Utterberg et al. ..... 604/513
5,456,668 A * 10/1995 Ogle, II ..... 604/110
5,533,975 A * 7/1996 Lu ..... 604/110
5,752,936 A * 5/1998 Chen ..... 604/110
5,800,403 A * 9/1998 Pressly et al. ..... 604/195
5,993,419 A * 11/1999 Lo et al. ..... 604/110
6,074,370 A * 6/2000 Pressly et al. ..... 604/195
6,090,077 A * 7/2000 Shaw ..... 604/195
6,096,005 A * 8/2000 Botich et al. ..... 604/110
6,099,500 A * 8/2000 Dysarz ..... 604/110
6,117,113 A * 9/2000 Novacek et al. ..... 604/195
6,241,707 B1 * 6/2001 Dysarz ..... 604/110

* cited by examiner

FLUID COLLECTION DEVICE HAVING TILTING RETRACTABLE NEEDLE

Matter enclosed in heavy brackets [ ] appears in the original patent but forms no part of this reissue specification; matter printed in italics indicates the additions made by reissue.

FIELD OF THE INVENTION

The present invention relates to fluid collection devices for sampling fluid from a patient. More specifically, the invention relates to such a device having a retractable needle feature for rendering the device non-reusable and safely disposable.

BACKGROUND OF THE INVENTION

Various types of medical devices employ a needle for piercing the skin of a patient for diagnostic or therapeutic purposes. One such device is a phlebotomy or blond collection device that includes a needle for piercing a blood vessel of the patient to allow blood to be sampled from the patient. When the needle is inserted into the blood vessel of the patient, blood is withdrawn through the needle into a vacuum collection tube. Handling of such needle-bearing medical devices after the needle is withdrawn from the patient can result in transmission of various pathogens, most notably human immune virus (HIV), to uninfected medical personnel, due to an inadvertent needle stick.

Since the mid-1980s, concern over the risk of accidental needle stick injuries has spawned a number of design approaches fur safety needle devices. Such devices can be broadly categorized as sliding sheath needle devices, wherein a physical barrier is positioned about the needle tip after use, and as needle-retraction devices, wherein the tip of the needle is retracted into the device after use.

The known devices suffer from one of several problems, including complicated structures that increase the cost of manufacturing the device. A safety needle product may be safe, but if it is too expensive, it will not be accepted, and the benefits of the safety product will never be recognized by the medical community. In addition, many devices require awkward or cumbersome actions to cause the needle to retract. The more complicated it is to retract a needle, the less likely it is that the medical professional will take the time to retract the needle, particularly in emergency situations.

In addition, in the field of phlebotomy, many of the known devices do not adequately protect against inadvertent contact with the non-patient tip of the needle. Since a person's finger is generally smaller than the rearward opening of a phlebotomy device, the rearward end of the needle remains a safety concern after it has been contaminated with a patient's blood. The known medical devices do not adequately address the protection needed to efficiently shield both the forward and rearward ends of the needle.

SUMMARY OF THE INVENTION

In light of the foregoing, the present invention provides a safety medical device having a retractable needle. The present invention is particularly suited for operation in connection with a fluid container such as a vacuum tube used for phlebotomy. The device includes a needle having a sharpened tip for piercing a patient. Preferably, the needle is double-ended having a rearward sharpened tip for piercing a seal on a fluid container. After use, the needle is retracted into the housing of the device so that the forward end of the needle is enclosed to prevent inadvertent contact with the contaminated needle.

The invention includes a biasing element such as a spring that biases the needle rearwardly toward the retracted position in which the needle is enclosed within the housing. The needle retainer releasably retains the needle against the bias of the spring so that the forward tip of the needle is exposed for use. After use, the medical professional actuates retraction to release the needle so that the spring displaces the needle rearwardly into the retracted position.

Another object of the invention is to provide a guide for guiding the needle when the needle is displaced between the projecting position and the retracted position. The guide includes at least one track and at least one guide tab connected with the needle, and projecting into operative engagement with the track. The track has an axial portion extending substantially parallel to the axis of the housing and a transverse portion extending transverse the axis of the barrel so that during retraction the needle is tilted so that the needle is disposed transverse the axis of the housing in the retracted position.

Yet another object of the invention is to provide a pocket for receiving and protecting the rearward sharpened tip of the needle when the needle is disposed in the retracted position. The pocket may be formed in a cylindrical insert that lines the housing. Preferably, the insert further includes a wing projecting forwardly and intersecting the guide. The wing has a lower edge configured in the shape of the transverse portion of the track, wherein the lower edge of the wing forms a sidewall of the transverse portion of the track.

BRIEF DESCRIPTION OF THE DRAWINGS

The foregoing summary as well as the detailed description below will be better understood when read in conjunction with the drawings, in which.

DETAILED DESCRIPTION OF THE PREFERRED EMBODIMENTS

Figure 1:
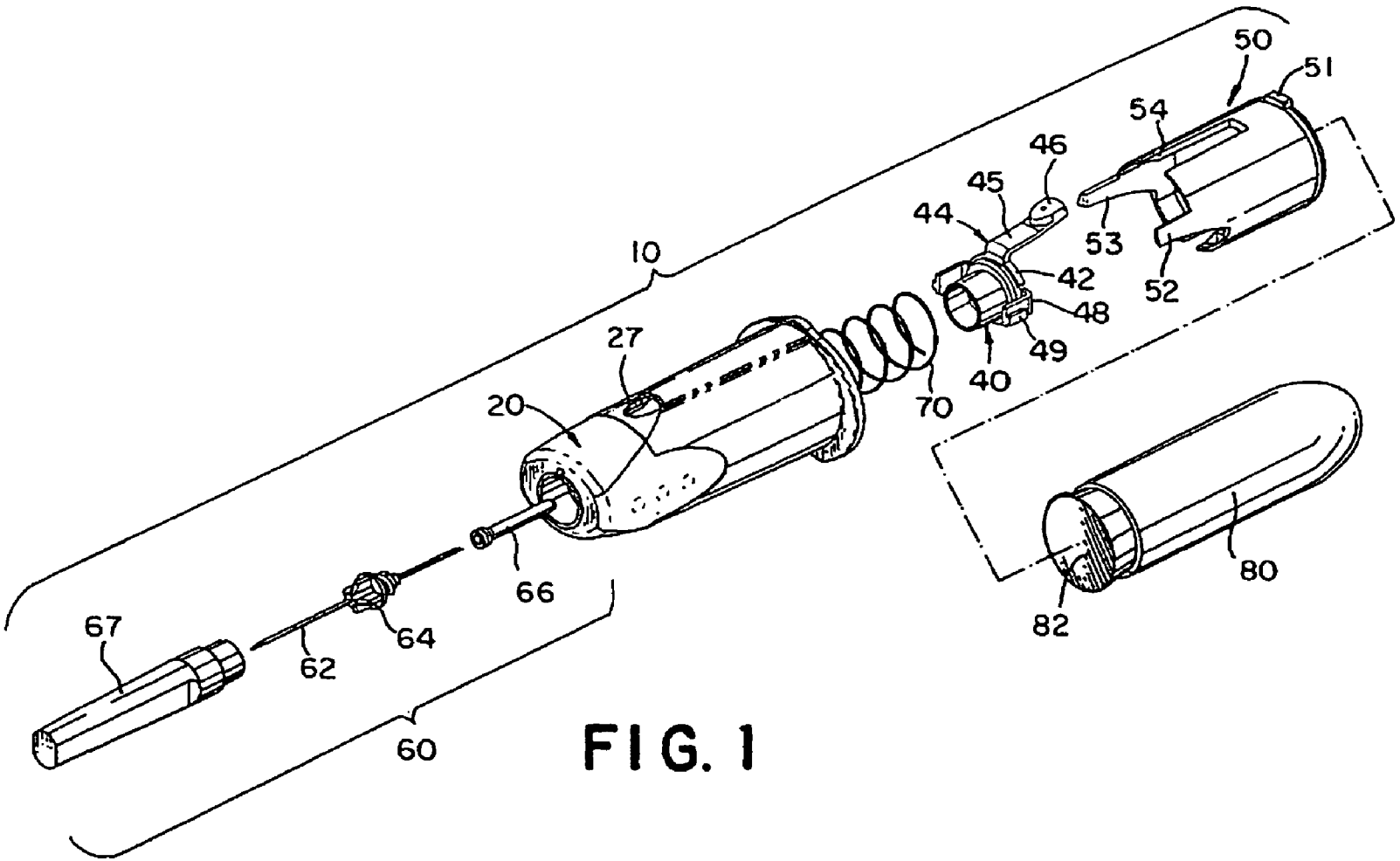
FIG. 1 is an exploded perspective view of a medical device having a retractable needle manifesting aspects of the present invention.

Referring to the drawings in general, and to FIG. 1 specifically, a needle-bearing medical device is designated generally 10. The device 10 is operable in connection with a fluid container 80, such as a fluid sampling container for use in drawing blood samples. The device 10 includes a double ended needle 62. The forward end of the needle is inserted into the patient and the rearward end of the needle pierces a seal 82 on the container 80. After use, the container is removed, and if desired, further containers 80 are used to take further samples while the forward end of the needle remains in the patient. After the last container 80 is removed, the needle is retracted into the device 10 to protect against inadvertent contact with the contaminated needle.

Figure 4:
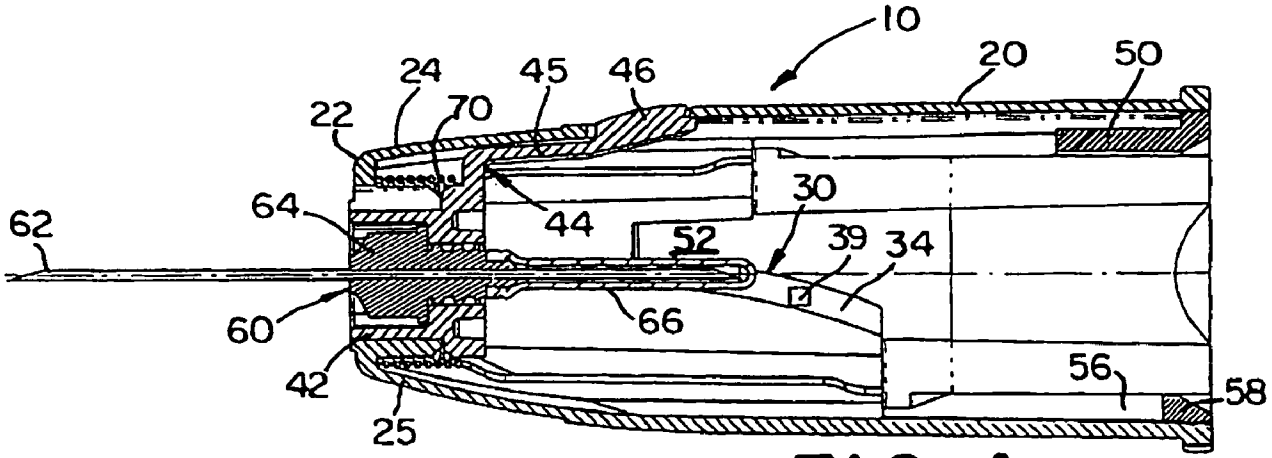
FIG. 4 is a side cross-sectional view of the medical device illustrated in FIG. 1.
Figure 5:
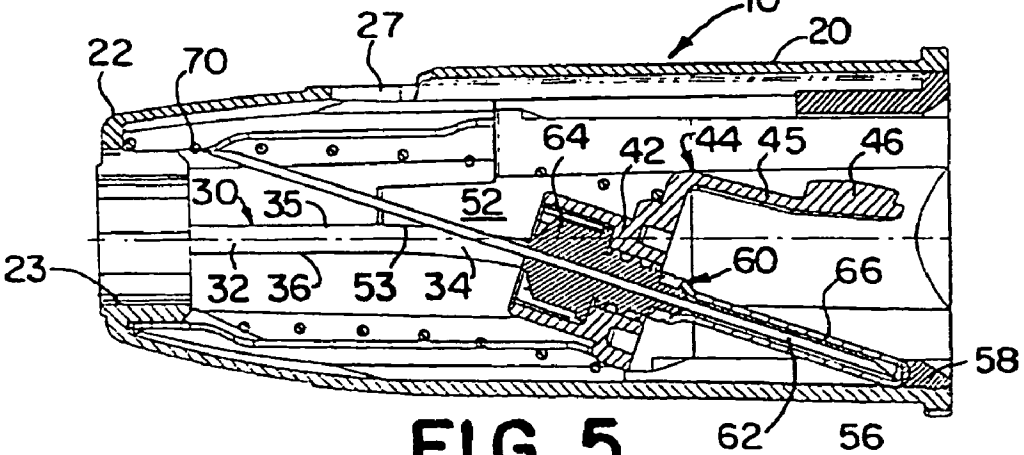
FIG. 5 is a side cross-sectional view of the medical device illustrated in FIG. 1, showing the needle in a retracted position.

As shown in FIG. 1, the device includes five elements or subassemblies: a needle assembly 60, a substantially hollow barrel 20, a spring 70, a needle holder 40, and an insert 50. Referring to FIG. 4, the needle 62 projects forwardly from the forward end of the barrel. The spring 70 biases the needle rearwardly, while the needle holder 40 releasably retains the needle 62 against the rearward bias of the spring 70. The needle holder 40 includes a needle retainer 44 having a push-button 46 operable by the medical professional using the device 10. After use, the medical professional depresses the button 46 to retract the needle. After the button is pressed, the spring displaces the needle holder 40 and needle 62 rearwardly. As the needle is retracted, a guide track 30 formed in the interior wall of the barrel 20 guides the needle so that the needle tilts off-axis, as shown in FIG. 5.

The details of the barrel 20 will now be described more fully with reference to FIGS. 1, 2, 4 and 6. The barrel is a hollow, generally cylindrical element having an open rearward end for receiving the fluid container 80. The forward end tapers radially inwardly forming a nose 22 having an opening 23 for receiving the needle assembly 60. The nose 22 can be formed so that it tapers inwardly around the entire circumference of the barrel. However, as shown in FIG. 1, the sides of the nose generally do not taper radially inwardly. Instead, only the top and bottom surfaces of the barrel taper inwardly forming a flattened wedge-shaped nose 22.

In this way, the nose 22 has a top face 24 and a bottom face 25. The two faces 24, 25 may be curved circumferentially as shown in FIG. 1, and, preferably the radius of curvature of the top and bottom faces is significantly larger than the radius of curvature of the side portions of the nose. In addition, preferably, the bottom face 25 tapers inwardly at a greater angle relative to the central barrel axis than the top face 25, as can be seen in FIG. 4.

As shown in FIG. 4, an annular support collar 26 intersects the nose opening 23 forming a reduced diameter cylindrical bore within the nose 22. The support collar 26 aligns the needle assembly 60 with the needle holder 40 and supports the needle assembly and the needle holder.

A plurality of circumferentially spaced axially elongated ribs 28 are provided for aligning the fluid container 80 when it is inserted into the device to ensure that the container is substantially centered within the housing so that the rearward end of the needle pierces the seal of the container. The ribs 28 are integrally formed with the barrel 20 so that the ribs protrude radially inwardly from the inner surface of the barrel.

Figures 2, 6, 7, 8:
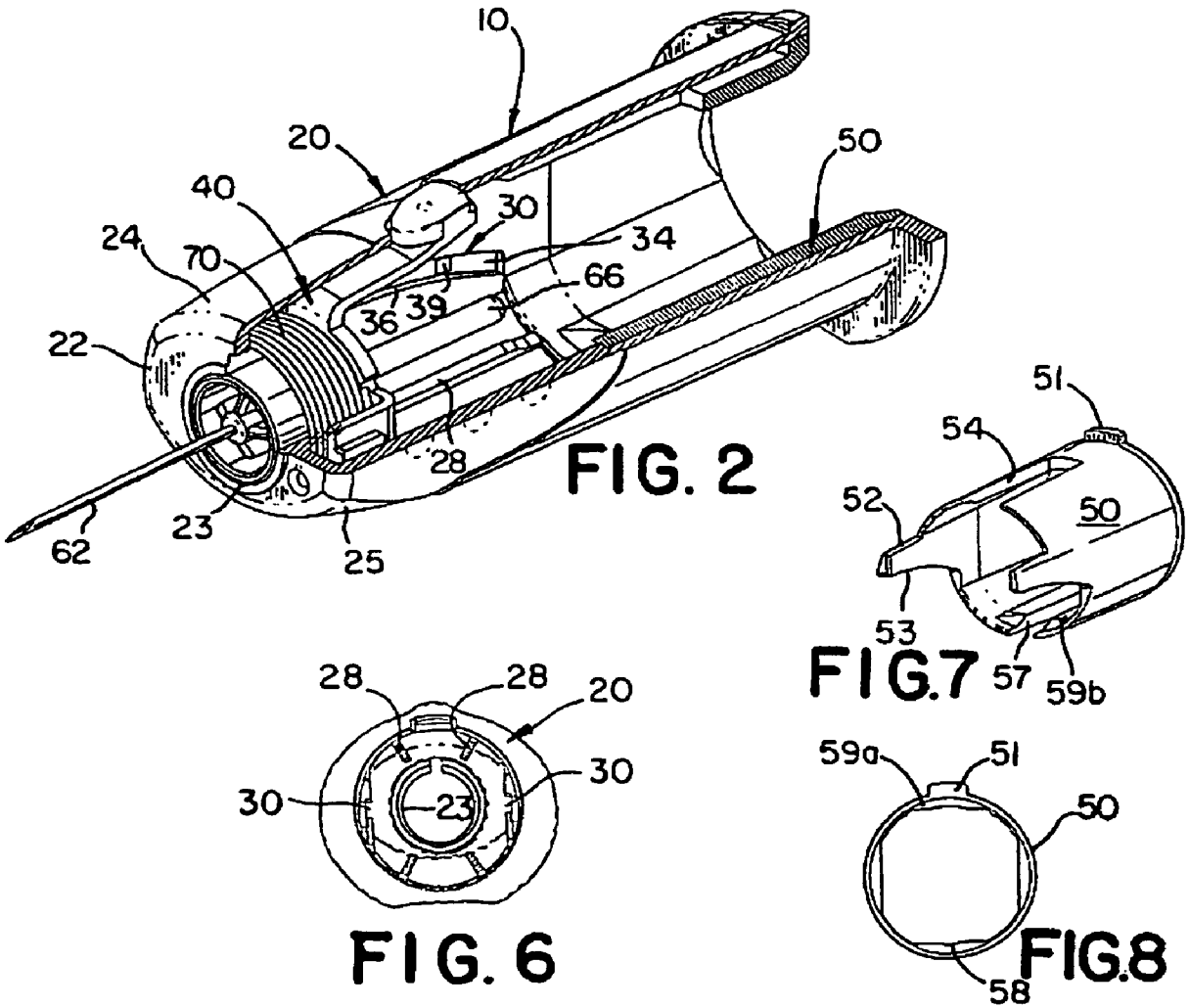
FIG. 2 is a perspective view of the medical device illustrated in FIG. 1, partially in section.
FIG. 6 is a right-side view of the barrel of the medical device illustrated in FIG. 1.
FIG. 7 is a perspective view of an insert forming part of the medical device illustrated in FIG. 1.
FIG. 8 is a right-side view of the insert illustrated in FIG. 7.

The interior wall of the barrel is relieved to form a recess for receiving the insert 50. More specifically, the barrel is relieved in a shape to cooperate with the shape and thickness of the insert 50 to form a smooth wall transition between the interior of the insert 50 and the interior of the barrel 20 as shown in FIGS. 2 and 4. An alignment key 51 shown in FIG. 1, integrally formed at the rearward end of the insert 50 cooperates with a recess formed at the rearward end of the barrel to circumferentially align the insert relative to the barrel.

The barrel 20 further includes a pair of guide tracks 30 formed in its inner wall, which guide the needle assembly 60 and needle bolder 40 during retraction. Preferably, the guide tracks 30 are disposed in opposing relation and are substantially a mirror of one another about the central axis of the device 10. Each guide track 30 comprises a groove support channel formed in the barrel wall. However, if desired, the guide tracks can be slots through the wall instead of grooves. In addition, although the device is described as having a pair of guide tracks, the device can be configured to use only a single guide track formed in the barrel.

The guide track 30 includes two portions, an axial portion 32 extending substantially parallel to the central axis of the device, and a transverse portion 34 intersecting the axial portion and extending transverse the central axis of the device. The groove of the guide track 30 has an upper wall 35 and a lower wall 36. The groove can be formed so that the upper and lower walls 35, 36 extend along the entire length of the axial portion 32 and the transverse portion 34. However, as described further below, the barrel 20 can be molded more efficiently if one of the track walls 35, 36 does not extend along the entire length of the track.

Specifically, in the present instance, the upper wall 35 of the guide track 30 extends along the axial portion 32 but does not extend along the entire length of the transverse portion 34. The height of the upper wall 35 reduces along the length of the transverse portion 34 to a point at which there is no longer an upper wall 35 of the groove formed in the barrel. In other words, the upper wall 35 feathers out into a recess formed in the barrel for receiving the insert 50, which has a pair of wings 52. These wings 52 form the upper wall of the groove along the transverse portion 34 as discussed further below.

Referring to FIG. 7, the insert 50 is a hollow, generally cylindrical element. The insert 50 is separately formed from the barrel 20 and then preferably fixedly connected with the barrel. The insert 50 may be connected to the barrel in a variety of ways, such as adhesive or ultrasonic welding. However, in the present instance, the insert and barrel are snap fit together. Specifically, a circumferential rib projecting radially outwardly from the outer surface of the rearward end of the insert engages an annular groove in the interior wall of the rearward end of the barrel.

Figure 3:
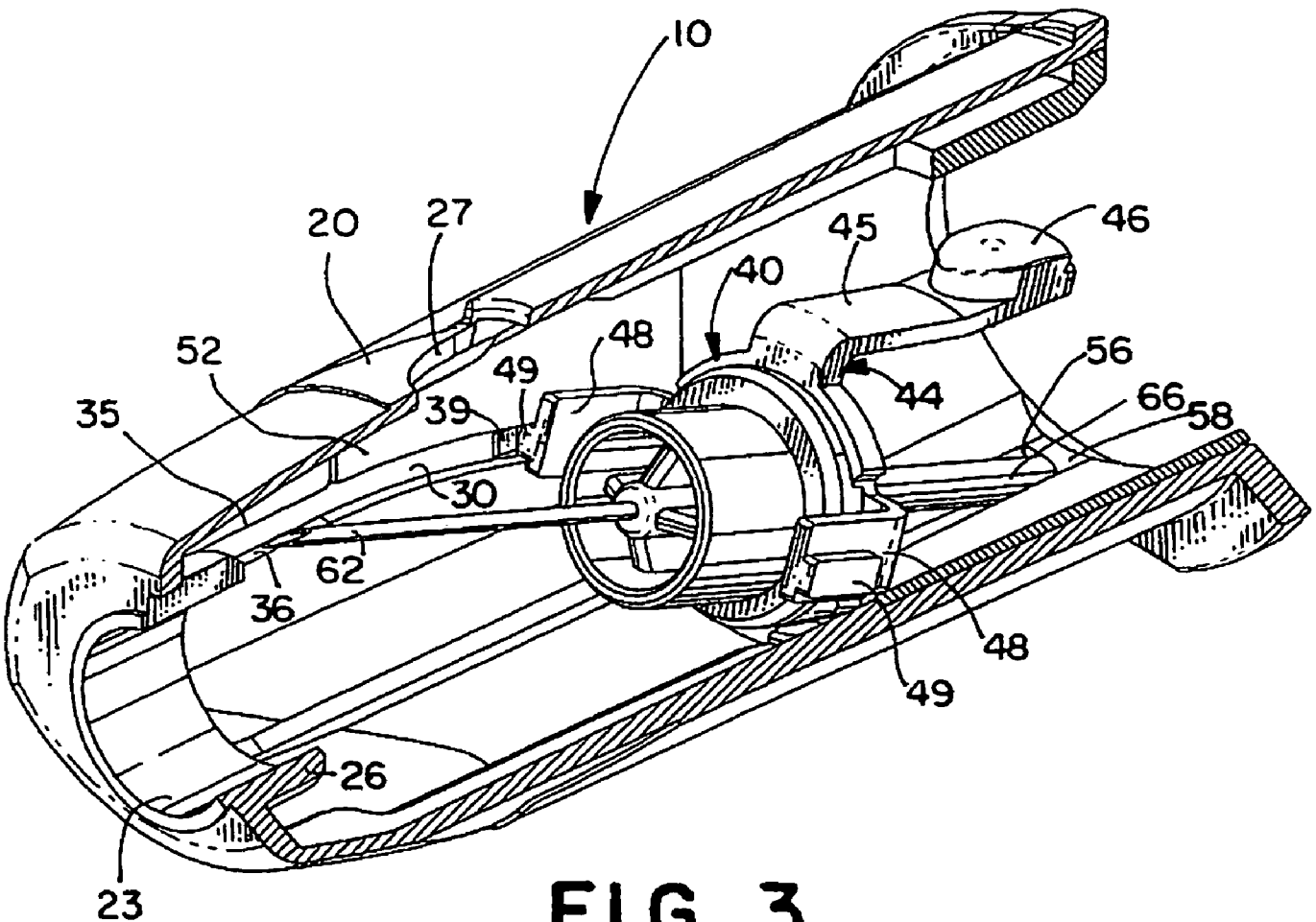
FIG. 3 is a perspective view of the medical device illustrated in FIG. 1, partially in section, showing the needle in a retracted position.

A pair of axially elongated slots 54, 57 extend rearwardly from the forward end of the insert, terminating adjacent the rearward end of the insert. The first slot 54 is located on the upper half of the insert, and provides clearance for the needle holder 40 as the needle is retracted, so that the insert does not interfere with the needle holder, which would impede retraction as can be seen in FIGS. 4, 5 and 7. The second slot 57 is located on the lower half of the insert 50, opposing the first slot 54. The rear wall 58 at the terminal end of the lower slot 57, together with the walls of the lower slot, form a pocket 56 for protecting the rearward end of the needle after the needle is retracted, as shown in FIGS. 3, 5.

The interior of the insert is configured to form a socket for receiving the fluid container 80. Specifically, the interior of the insert 50 is configured to locate and center the fluid container to minimize lateral movement of the fluid container within the device 10. As shown in FIGS. 7-8, the interior sidewalls of the insert have substantially planer portions that projects inwardly from the generally curved interior surface of the insert. The upper and lower interior walls have axially elongated ribs 59a, 59b that straddle the upper and lower slots 54, 57 projecting radially inwardly from the generally curved interior surface of the insert.

A pair of opposing wings 52 project forwardly from the forward end of the body of the insert. The wings are substantially parallel to one another and the central axis of the insert, opposing one another. The wings 52 preferably have a thickness that is substantially similar to the depth of the guide track 30 groove. The lower edge 53 of each wing 52 forms a curve having a shape or curvature similar to the transverse portion 34 of the guide track 30.

As discussed previously, the groove that forms the rearward end of the guide track formed in the barrel opens up because the upper wall of the transverse portion of the groove feathers out into a recess in the barrel so that there is no upper wall. Instead, the lower edge 53 of the wings 52 form the upper wall 35 of the guide track 30 along the transverse portion 34 of the guide track as follows.

During assembly, the insert 50 is aligned with and connected to the barrel 20 so that the lower edge 53 of each arms is circumferentially spaced apart from the lower wall 36 of the guide track along the transverse portion 34. The insert is located so that the configuration of the lower edge 53 of each arm 52 is substantially parallel to the lower wall 36 of the transverse portion 34 of the guide track groove. In this way, the transverse portion 34 of the guide track is formed by the lower edge 53 of each wing arm 52 and the open groove formed in the interior surface of the barrel 20.

Referring now to FIGS. 1 and 4, the details of the needle holder 40 will be described in greater detail. The needle holder 40 is configured to cooperate with the needle assembly 60. The needle holder includes a generally cylindrical central hub 42, a needle retainer 44 projecting radially outwardly from the hub and a pair of opposing guide arms 48 projecting outwardly from the hub. The hub 42 is hollow, having a bore for receiving the needle assembly 60.

The guide arms 48 cooperate with the guide track 30 to guide the needle holder during retraction. Specifically, the guide arms project radially outwardly from the hub 42 opposing one another. The terminal end of each guide arm 48 forms a tab 49 configured to cooperate with the channel of the guide track 30. The guide tab 49 projects into the groove of the guide track 30 so that during retraction the guide arm 48 and the attached hub 42 follow the track. The guide arms 48 are radially deformable, and may be formed so that the guide arms are biased radially outwardly to ensure that the labs 49 engage the guide tracks 30.

As shown in FIGS. 4, 5, the needle holder 40 is operable between an extended position and a retracted position. In the extended position, the needle holder hub 42 is located within and supported by the support collar 26 located inside the forward end of the barrel. The support collar centers the needle holder and the attached needle assembly 60 so that the needle assembly is substantially centered in the barrel and the needle is substantially parallel to the central axis of the barrel. In the retracted position, the needle holder 40 and attached needle assembly 60 are displaced rearwardly into the barrel 20.

The spring 70 is a coil spring circumscribing the needle 62. The forward end of the spring bears against the forward end of the barrel 20 and the rearward end of the spring bears against the needle holder 40.

The needle retainer 44 attached to the hub 42 releasably retains the needle against the rearward bias of the spring 70. The needle retainer comprises an elongated radially deformable arm 45 and a button or latch 46 integrally formed at the terminal end of the arm. Preferably, the needle retainer is molded so that the arm is biased radially outwardly to bias the button 46 into engagement with an aperture 27 in the barrel 20. The button 46 operates as a latch engaging the rim of the aperture 27 in the barrel. The button 46 projects into the aperture so that it is exposed for manual actuation by the medical professional.

The needle may be fixedly attached to the needle holder 40 during manufacture. However, preferably the needle is configured as an element of a separate needle assembly 60 so that it can be attached to the needle holder either by the manufacturer or by the medical professional prior to use. In the present instance, the needle assembly includes a double ended needle 62, a hub 64, a forward needle cover 68 and a pierceable needle cover 67 that covers the rearward end of the needle. The needle hub 64 is configured to cooperate with the needle holder 40 to attach the needle assembly 60 to the needle holder. For instance, the needle hub 64 may include external threads that the threadedly engage internal threads in the bore of the needle holder 40. However, in the present instance, the needle hub 64 and the needle holder 40 are connected by an interference or friction fit.

The needle hub 64 includes a bore through which the needle 62 extends, and the needle hub is bonded to the needle by adhesive. The rearward end of the needle hub 64 forms a barb for attaching the needle cover 66 to the needle hub. The rear needle cover 66 is formed of a pierceable resealable elastomeric material. The forward needle cover 67 is formed of a hard plastic.

As shown in FIG. 4, prior to use the rear needle cover 67 encloses the rearward end of the needle. During use, a fluid container 80 is inserted into the device so that the rearward end of the needle pierces a seal 82 on the fluid container. As the fluid container is mounted on the needle, the fluid container seal 82 compresses the needle seal 66 along the length of the needle. As the fluid container compresses the needle seal, the needle pierces the rear needle cover and then pierces the fluid container seal. When the fluid container is removed, the rear needle cover resiliently rebounds to re-extend over the needle to form a fluid-tight seal over the rearward end of the needle. This prevents fluid from leaking out the rearward end of the needle when a fluid container is not engaged.

Configured as described above, the device 10 operates as follows. The medical professional connects the needle assembly to the needle holder 40 by attaching the needle hub 64 to the needle holder hub 42. After the needle assembly 60 is attached, the forward needle cover 67 is removed. This is the configuration of the device 10 prior to use illustrated in FIG. 4.

The medical professional then inserts the needle into a patient's vein and then inserts a vacuum tube 80 into the rearward end of the barrel and displaces the vacuum tube forwardly until the needle pierces the seal 82 of the vacuum tube and the forward end of the tube is seated against the needle holder hub 42. Blood flows from the patient into the vacuum tube 80.

Frequently multiple samples are taken. In such situations, the first vacuum tube is removed from the device. After removing the vacuum tube, the needle cover 66 extends over the rearward end of the needle to seal the needle so that blood does not continue to flow from the patient through the needle and leak out the back end of the needle while there is no vacuum tube mounted in the device. Further samples can be taken in a plurality of vacuum tubes in a manner similar to that as described above, while the needle remains in the patient.

After the final sample is taken, the medical professional removes the last vacuum tube. The used needle is contaminated with the patient's blood so it should be shielded to prevent an accidental needle stick. Accordingly, the medical professional actuates retraction to shield the needle.

Specifically, the medical professional presses the button 46 inwardly, so that the button disengages the locking aperture 27 in the barrel. As the button 46 is pressed, the needle retainer arm 45 deforms radially inwardly. Once the button disengages the locking aperture, the spring 70 displaces the needle rearwardly.

As the spring retracts the needle, the needle holder 40 follows the guide track 30. During the first part of retraction, the needle is displaced rearwardly parallel to the central axis of the barrel. The upper slot 54 in the insert 50 and an axial groove in the top of the barrel 20 provide clearance for the needle retainer arm 45 and button 46 as they are retracted rearwardly. After the guide arms 48 of the needle holder engages the transverse portion 34 of the guide track 30, continued rearward displacement displaces the needle rearwardly, while simultaneously tilting the needle away from the central axis of the barrel.

As shown in FIG. 5, preferably the diameter of the spring 70 is sufficiently large so that as the needle tilts, the forward tip of the needle stays within the interior of the spring so that the needle does not engage the spring, which could impede retraction. For this reason, the needle is laterally offset from the centerline of the spring. As shown in FIG. 4, in the extended position, the needle assembly 60 is closer to the bottom of the spring than the top of the spring. In this way, a needle can tilt through a greater angle for a given diameter spring without interfering with the spring.

At the end of retraction, the rearward edge of the guide tabs 49 engage a shoulder on the insert that forms the rear wall of the guide tracks 30. The end wall operates as a stop limiting rearward displacement of the needle assembly 60.

Since both ends of the needle are sharpened, is desirable to protect both ends of the needle against inadvertent contact. In addition, since the rear opening of the barrel is larger than an average person's finger, simply retracting the needle rearwardly may not adequately protect against the risk of contacting the rearward end of the needle. Accordingly, preferably, the needle is tilted off axis, as described above. In addition, preferably, the rear tip of the retracted needle is protected as discussed further below.

As described previously, a pocket is formed at the rearward end of the barrel. The pocket 56 is formed by the insert, which has a lower slot 57 terminating in an end wall 58. The transverse portion 34 of the guide tracks are aligned with the slot and the pocket 56. Accordingly, rearward displacement of the needle displaces the rearward tip of the needle into the pocket so that the pocket 56 shields the rear tip of the needle. Specifically, the rear needle tip is displaced into the slot 54 and behind the end wall 58, which prevent inadvertent contact with the contaminated needle. The device 10 can then be safely discarded.

Since the needle is tilted off-axis, the needle cannot be readily re-extended. However, it is desirable to include a lock or stop for impeding forward displacement of the needle after retraction to prevent re-extension of the contaminated needle.

Accordingly, the device includes a stop 39 disposed in at least one, and preferably both of the guide tracks 30 adjacent the rearward end of each guide track. The forward face of each stop 39 is tapered forming a ramp. The rearward face of each stop forms a shoulder that is substantially perpendicular to the guide track. As the needle is retracted, the guide tabs 49 ride in the guide track. The guide tabs are mounted on guide arms, which are flexible. Therefore, near the end of retraction, the guide tabs ride up the tapered face of the corresponding stop 39. As the guide tabs ride up the ramps, the arms 48 deflect radially inwardly. After the guide labs ride over the stops, the guide tabs snap back into the guide tracks. Since the rearward face of each stop 39 forms a shoulder, the stops engage the guide tabs to impede re-extending the needle 62 after retraction.

The terms and expressions which have been employed are used as terms of description and not of limitation. There is no intention in the use of such terms and expressions of excluding any equivalents of the features shown and described or portions thereof. It will be recognized by those skilled in the art that changes or modifications may be made to the above-described embodiments without departing from the broad inventive concepts of the invention. For instance, as described above, the pocket 56 that protects the rear needle tip is formed from the lower slot walls 57 and the end wall 58. However, the slot could be eliminated so that the pocket is formed simply by a lip projecting radially inwardly that prevents contact with the sharpened tip. It should therefore be understood that this invention is not limited to the particular embodiments shown and described herein, but is intended to include all changes and modifications that are within the scope and spirit of the invention as set forth in the claims.

What is claimed is:

1. A medical device operable in connection with a fluid container, comprising:

a housing having a rearward opening forming a socket configured to receive the fluid container;

a double-ended needle having a forward sharpened tip and a rearward sharpened tip operable between a projecting position in which the forward sharpened tip projects forwardly from the housing and a retracted position in which the forward sharpened tip is enclosed within the housing;

a biasing element biasing the needle rearwardly;

a guide for guiding the needle when the needle is displaced between the projecting position and the retracted position, comprising:

a track having an axial portion extending substantially parallel to the axis of the housing and a transverse portion extending transverse the axis of the housing; and a guide tab connected with the needle and projecting into operative engagement with the track;

a needle retainer releasably retaining the needle against the bias of the [spring] *biasing element* wherein upon actuation of the needle retainer, the needle is released so that the biasing element displaces the needle rearwardly into the retracted position and the guide guides the needle during retraction so that the needle is tilted transverse the axis of the barrel in the retracted position; *and* a generally cylindrical insert lining the interior of the rearward portion of the housing, comprising:

a pocket formed in the wall of the insert for receiving and protecting the rearward needle tip when the needle is disposed in the retracted position; *and* a guide arm projecting forwardly and intersecting the track, the guide arm having a lower edge configured in the shape of the transverse portion of the track, wherein the lower edge of the guide arm forms a sidewall of the transverse portion of the track.

2. The device of claim 1 comprising a button having a manually actable surface for actuating the needle retainer.

3. The device of claim 1 wherein the [spring] *biasing element* circumscribes the needle while the needle is disposed parallel to the axis of the housing and also while the needle is disposed transverse the axis of the housing in the retracted position.

4. The device of claim 1 comprising a resiliently flexible pierceable cover covering and sealing the rearward needle tip so that upon inserting the fluid container into the housing, the rearward sharpened needle tip pierces the cover and the fluid container deforms the cover, wherein upon removing the fluid container, the cover resiliently extends to cover and seal the rearward needle tip to prevent fluid front leaking out the rearward needle tip.

5. The device of claim 1 wherein the track comprises a groove formed in the interior wall of the housing.

6. The device of claim 1 wherein the housing comprises a locking aperture and the needle retainer comprises a radially deformable arm having a latch releasably engaging the locking aperture.

7. The device of claim 1 comprising a lock for locking the needle in the retracted position.

8. The device of claim [1] *7* wherein the lock comprises a stop spaced from the rearward end of the track.

9. The device of claim 1 wherein the pocket is aligned with the transverse portion of the track.

10. The device of claim 1 comprising a second guide substantially similar to the first guide, spaced apart from and opposing the first guide.

11. A medical device operable in connection with a fluid container, comprising:

a housing having a rearward opening forming a socket configured to receive the fluid container;

a double-ended needle having a forward sharpened tip and a rearward sharpened tip operable between a projecting position in which the forward sharpened tip projects forwardly from the housing and a retracted position in which the forward sharpened tip is enclosed within the housing;

a biasing element biasing the needle rearwardly;

a guide for guiding the needle when the needle is displaced between the projecting position and the retracted position, comprising:

a track having an axial portion extending substantially parallel to the axis of the housing and a transverse portion extending transverse the axis of the housing; and a guide tab connected with the needle and projecting into operative engagement with the track;

a needle retainer releasably retaining the needle against the bias of the biasing element wherein upon actuation of the needle retainer, the needle is released so that the biasing element displaces the needle rearwardly into the retracted position, and the guide guides the needle during retraction so that the needle is tilted transverse the axis of the barrel in the retracted position.

12. The device of claim 11 comprising a pocket adjacent the rearward end of the housing for receiving and shielding the rearward sharpened needle when the needle is disposed in the retracted position.

13. The device of claim 11 comprising a button having a manually actable surface for actuating the needle retainer.

14. The device of claim 11 wherein the [spring] *biasing element* circumscribes the needle while the needle is disposed parallel to the axis of the housing and also while the needle is disposed transverse the axis of the housing in the retracted position.

15. The device of claim 11 comprising a resiliently flexible pierceable cover covering and sealing the rearward needle tip so that upon inserting the fluid container into the housing, the rearward sharpened needle tip pierces the cover and the fluid container to deform the cover, wherein upon removing the fluid container, the cover resiliently extends to cover and seal the rearward needle tip to prevent fluid from leaking out the rearward needle tip.

16. The device of claim 11 wherein the track comprises a groove formed in the interior wall of the housing.

17. The device of claim 11 wherein the housing comprises a locking aperture and the needle retainer comprises a radially deformable arm having a latch releasably engaging the locking aperture.

18. The device of claim [11] *17* comprising a lock for locking the needle in the retracted position.

19. The device of claim [11] *18* wherein the lock comprises a stop spaced from the rearward end of the track.

20. The device of claim [11] *12* wherein the pocket is aligned with the transverse portion of the track.

21. The device of claim 11 comprising a second guide substantially similar to the first guide, spaced apart from and opposing the first guide.

22. A medical device operable in connection with a fluid container, comprising:

a housing having a rearward opening forming a socket configured to receive the fluid container, a needle having a forward sharpened tip operable between a projecting position in which the forward sharpened tip projects forwardly from the housing and a retracted position in which the forward sharpened tip is enclosed within the housing;

a biasing element biasing the needle rearwardly;

a *first* guide for guiding the needle when the needle is displaced between the projecting position and the retracted position*:* wherein the guide comprises a track and a follower attached to the needle and in operative engagement with the track, and a needle retainer releasably retaining the needle against the bias of the biasing element wherein upon actuation of the needle retainer, the needle is released so that the biasing element displaces the needle rearwardly into the retracted position, and the guide guides the needle during retraction, pivoting the needle so that the needle is tilted transverse the axis of the barrel in the retracted position*;* and

*a second guide substantially similar to the first guide, spaced apart from and opposing the first guide.*

23. The device of claim 22 wherein the needle comprises a rearward sharpened tip, and the device comprises a pocket disposed adjacent the rearward end of the housing for receiving and protecting the rearward needle tip to protect against inadvertent contact with the rearward needle tip.

24. The device of claim 23 wherein the pocket is aligned with the track.

25. The device of claim 22 comprising a button having a manually actable surface for actuating the needle retainer.

26. The device of claim 22 wherein the device comprises a needle hub attached to the needle, and the [spring] *biasing element* circumscribes substantially the length of the needle forward of the needle hub while the needle is disposed parallel to the axis of the housing and also while the needle is disposed transverse the axis of the housing in the retracted position.

27. The device of claim 22 wherein the needle comprises a rearward sharpened tip, and the device comprises a resiliently flexible pierceable cover covering and sealing the rearward needle tip so that upon inserting the fluid container into the housing, the rearward sharpened needle tip pierces the cover and the fluid container deforms the cover, wherein upon removing the fluid container, the cover resiliently extends to cover and seal the rearward needle tip to prevent fluid from leaking out the rearward needle tip.

28. The device of claim 22 wherein the track comprises a groove formed in the interior wall of the housing.

29. The device of claim 22 wherein the housing comprises a locking aperture and the needle retainer comprises a radially deformable arm having a latch releasably engaging the locking aperture.

30. The device of claim 22 comprising a lock for locking the needle in the retracted position.

31. The device of claim [22] *30* wherein the lock comprises a stop spaced from the rearward end of the track.

[32. The device of claim 22 comprising a second guide substantially similar to the first guide, spaced apart from and opposing the first guide.]

[33. The device of claim 23 wherein the pocket is aligned with the track.]

* * * * *